United States Patent
Bignozzi et al.

(10) Patent No.: US 12,208,072 B2
(45) Date of Patent: Jan. 28, 2025

(54) COMPOSITIONS FOR REMOVING NECROTIC OR INFECTED TISSUES FROM BODY SURFACE LESIONS AND FROM ORAL CAVITY

(71) Applicant: DEBx Medical Holding B.V., Rotterdam (NL)

(72) Inventors: Carlo Alberto Bignozzi, Ferrara (IT); Francesco Carinci, Bologna (IT); Alberto Cogo, Vicenza (IT)

(73) Assignee: DEBx Medical Holding B.V., Rotterdam (NL)

( * ) Notice: Subject to any disclaimer, the term of this patent is extended or adjusted under 35 U.S.C. 154(b) by 756 days.

(21) Appl. No.: 17/436,687

(22) PCT Filed: Feb. 13, 2019

(86) PCT No.: PCT/IB2019/051146
§ 371 (c)(1),
(2) Date: Sep. 7, 2021

(87) PCT Pub. No.: WO2020/165628
PCT Pub. Date: Aug. 20, 2020

(65) Prior Publication Data
US 2022/0401392 A1 Dec. 22, 2022

(51) Int. Cl.
*A61K 31/185* (2006.01)
*A61K 9/00* (2006.01)
(Continued)

(52) U.S. Cl.
CPC .......... *A61K 31/185* (2013.01); *A61K 9/0063* (2013.01); *A61K 31/10* (2013.01);
(Continued)

(58) Field of Classification Search
CPC .... A61K 31/10; A61K 31/185; A61K 31/191; A61K 31/194; A61K 31/198;
(Continued)

(56) References Cited

U.S. PATENT DOCUMENTS

| 5,939,090 A | 8/1999 | Beaurline et al. |
| 2004/0132810 A1 | 7/2004 | Basara |

(Continued)

FOREIGN PATENT DOCUMENTS

| CN | 1539422 A | 10/2004 |
| CN | 101475448 B | 8/2011 |

(Continued)

OTHER PUBLICATIONS

Minnesota Dept of Health, "*Staphylococcus aureus*", publ. 2010, p. 1 (Year: 2010).*

(Continued)

*Primary Examiner* — Sarah Pihonak
(74) *Attorney, Agent, or Firm* — N.V. Nederlandsch Octrooibureau

(57) ABSTRACT

A composition, usable for removing a biofilm and necrotic or infected tissues from skin lesions and lesions of the oral cavity, comprises methanesulfonic acid 99.0% and a proton acceptor. The proton acceptor is selected from the group consisting of: anhydrous sodium carbonate, 5-amino-2-mercaptobenzimidazole, ethylenediaminetetraacetic acid tetrasodium salt, sodium gluconate, sodium tartrate dihydrate, 2-mercapto-5-benzimidazole sodium sulfonate, dimethyl sulfoxide, polyethylene glycol 400, polyethylene glycol 600, silicon dioxide, tetraethoxysilane, and mixtures thereof. The aforesaid composition can be prepared in the form of a solution, gel or cream.

12 Claims, 2 Drawing Sheets

(51) Int. Cl.
    *A61K 31/10*         (2006.01)
    *A61K 31/191*       (2006.01)
    *A61K 31/194*       (2006.01)
    *A61K 31/198*       (2006.01)
    *A61K 31/4184*      (2006.01)
    *A61K 31/695*       (2006.01)
    *A61K 31/77*         (2006.01)
    *A61K 33/00*         (2006.01)
    *A61P 1/02*          (2006.01)
    *A61P 17/02*        (2006.01)
    *A61P 31/04*        (2006.01)
(52) U.S. Cl.
    CPC .......... *A61K 31/191* (2013.01); *A61K 31/194* (2013.01); *A61K 31/198* (2013.01); *A61K 31/4184* (2013.01); *A61K 31/695* (2013.01); *A61K 31/77* (2013.01); *A61K 33/00* (2013.01); *A61P 1/02* (2018.01); *A61P 17/02* (2018.01); *A61P 31/04* (2018.01)
(58) Field of Classification Search
    CPC .. A61K 31/4184; A61K 31/695; A61K 31/77; A61K 33/00; A61K 47/10; A61K 9/006; A61K 9/0063; A61K 9/06; A61K 9/08; A61K 45/06; A61P 1/02; A61P 17/02; A61P 31/00; A61P 31/04
    See application file for complete search history.

(56) References Cited

U.S. PATENT DOCUMENTS

| | | |
|---|---|---|
| 2005/0142208 A1 | 6/2005 | Yoo et al. |
| 2009/0202457 A1 | 8/2009 | Basara |
| 2013/0101627 A1 | 4/2013 | Tieu et al. |
| 2015/0152364 A1 | 6/2015 | Theyssen et al. |
| 2015/0283047 A1 | 10/2015 | Banowski et al. |
| 2015/0352023 A1 | 12/2015 | Berg et al. |
| 2015/0376726 A1 | 12/2015 | Bertkau et al. |
| 2016/0058718 A1 | 3/2016 | Basara et al. |
| 2017/0333400 A1 | 11/2017 | Johnson et al. |
| 2018/0093305 A1 | 4/2018 | Laffitte et al. |

FOREIGN PATENT DOCUMENTS

| | | |
|---|---|---|
| CN | 106309417 A | 1/2017 |
| CN | 107129575 A | 9/2017 |
| CN | 107827745 A | 3/2018 |
| EP | 3098282 A1 | 11/2016 |
| ES | 2633564 T3 | 9/2017 |
| FR | 2730934 A1 | 8/1996 |
| IN | 1879/ | 5/2015 |
| IN | 1879/MUM/2015 | 5/2015 |
| RU | 2571283 C2 | 12/2015 |
| RU | 2665951 C2 | 1/2017 |
| WO | 9731732 A1 | 9/1997 |
| WO | 2006030826 A1 | 3/2006 |
| WO | 2007002194 A2 | 1/2007 |
| WO | 2010138518 A2 | 12/2010 |
| WO | 2014/197584 A1 | 12/2014 |
| WO | 2017200979 A1 | 11/2017 |
| WO | 2018/146194 A1 | 8/2018 |
| WO | WO-2019067560 A1 * | 4/2019 ............. A01N 25/30 |

OTHER PUBLICATIONS

Anonymous: "Methanesulfonic acid—National Library of Medicine HSDB Database", Oct. 23, 2019.

Schwarzer, S., Radzieta, M., Jensen, S.O. and Malone, M., 2021. Efficacy of a topical wound agent methanesulfonic acid and dimethylsulfoxide on in vitro biofilms. International Journal of Molecular Sciences, 22(17), p. 9471.

Anonymous: "Lime and Rust Cleaner Record ID: 6021365 Company: Ceys Manufacturer", Mintel, Oct. 1, 2018 (Oct. 1, 2018), XP093185934, Retrieved from the Internet: URL:https://www.mintel.com/ Citation is not enclosed due to copyright restrictions.

Anonymous: "Record ID: 3403789 Company: Ideal Iron Descaler", Mintel, Aug. 1, 2015 (Aug. 1, 2015), XP093185936 Citation is not enclosed due to copyright restrictions.

* cited by examiner

COMPOSITIONS FOR REMOVING NECROTIC OR INFECTED TISSUES FROM BODY SURFACE LESIONS AND FROM ORAL CAVITY

FIELD OF THE INVENTION

The invention relates to compositions that are usable for removing necrotic or infected tissues from body surface lesions, in particular chronic wounds or ulcers, and from the oral cavity, in particular from periodontal pockets, peri-implant pockets or from wounds.

PRIOR ART

It is known that chronic wounds contain microorganisms, in particular bacteria, which replicate and cause a persistent inflammatory response. In particular, the so-called inflammatory cascade produces vasodilation and increases remarkably the haematic flow to the area of the lesion. In a chronic lesion, the continuous presence of virulent microorganisms leads to a massive and persistent inflammatory response, which at the end contributes to damaging the host organism. In fact, a persistent production of inflammation mediators and a constant migration of neutrophil granulocytes occur. The latter release cytolytic enzymes and free radicals in the wound, which are the main culprits for tissue damage. Further, the macrophages are inhibited with the consequent inability of the chronic lesion to self-regenerate. Localized thrombosis may also occur and metabolites are released with vasoconstricting action that may induce a tissue hypoxia, causing a further bacterial proliferation and tissue destruction. Due to the significant invasiveness of some infecting bacterial species, the microbial component can contribute to aggravating the lesions and increasing the layer of biofilm.

The term "biofilm" defines the thin layer of glycoproteic material that is produced by actively replicating bacteria and that adheres to the bed of the lesion. The biofilm that forms in an infected wound contributes to delaying the healing thereof. In the presence of biofilm, in fact, the conditions are created so that the single microorganisms interact reciprocally by exchanging nutrients and metabolites, so as to constitute proper organized bacterial communities. The biofilms thus act as protected foci of infection and bacterial resistance inside the wound and are able to protect the bacteria from the action of antimicrobial agents such as antibiotics and antiseptics. Normally, the biofilms consist of a plurality of layers of microorganisms and the communication between the microbial cells is a crucial factor for the purposes of the development and maintenance of the biofilm.

The term "chronic cutaneous ulcer" defines the skin lesions that do not progress to healing after at least six weeks of appropriate treatment. Regardless of the aetiology (in fact, diabetic, venous, arteriopathic, vascular and post-traumatic chronic ulcers exist), chronic cutaneous ulcers display some shared pathogenic mechanisms, which make them chronic. Of these pathogenic mechanisms, the most known are: the excessive presence of inflammatory proteins (cytokines and proteases) in the exudate; a persistent colonization of the bottom of the lesion by pathogenic microorganisms; the development of a biofilm that makes the bottom of the lesion inaccessible to drugs and medications. These features of the chronic cutaneous ulcer slow or stop the autolytic process of removal of the non-vital material, the proliferation of neovessels, which is indispensable for the formation of the granulation tissue, and the proliferation of the dermal and epidermal cells.

The chronic cutaneous ulcers, such as for example the chronic cutaneous ulcers of the lower limbs, are a worldwide problem. It is in fact estimated that 1.5% of the world's population is affected by this pathology. As the age is a significant risk factor, the prevalence of the aforesaid chronic cutaneous ulcers is low in children's age and very high in the old age. Also the socioeconomic class, to which the patient belongs, is a risk factor, so that the disease is more widespread in the developing Countries than in the economically more advanced Countries. As also the chronic comorbidities present in the aged population are a risk factor for the development of chronic cutaneous ulcers and as the average age of the population is increasing constantly, the incidence of the chronic cutaneous ulcers is expected to increase progressively in future years.

The therapeutic treatment of the chronic cutaneous ulcers requires an enormous financial commitment for the health systems. In the USA, about 2 million working days are lost each year because of chronic ulcers. Furthermore, the developed Countries spend about 3 to 5.5% of their total health budget on the treatment of the chronic cutaneous ulcers. The chronic cutaneous ulcers constitute a severe event for the patient, as these pathologies are associated with an increase in morbidity and mortality and are often accompanied by chronic pain that requires the use of major analgesics. Furthermore, the patient becomes dependent on the nursing care that he or she requires and this all entails a significant decline of the patient's quality of life.

It is by now a common conviction amongst the persons skilled in the art that in order to activate the process of healing of a chronic cutaneous ulcer a balance is necessary between the inflammatory process and the regenerative process, so as to take the ulcer to a state that is comparable to that of an acute ulcer. This effect is normally achieved through a known procedure, namely the debridement of the bottom of the ulcer. With this procedure, the non-vital tissues, the stratified secretions on the bottom of the lesion and possibly also the biofilm formed therein are removed surgically.

A drawback of the debridement is that in order for the latter to be effective it has to expose the vital tissue on all the bottom of the ulcer, which creates a significant risk of bleeding for the patient.

Another drawback of the debridement is that this procedure is of surgical type and thus requires the use of a suitably equipped operating theatre and the intervention of specialized staff (doctors and anaesthetists). Consequently, it is necessary to hospitalize the patient. However, the necessary hospitalization and the complexity of performing the debridement increase the costs associated with such a procedure and make this procedure accessible only for a minority of patients.

Non-surgical debridement methods are known, such as the administration of lytic enzyme-based ointments, the negative pressure therapy and some advanced medications. The non-surgical debridement methods, although substantially non-invasive, are unanimously judged as hardly effective or need long periods of application in order to be effective. Therefore there is a strong need to make the treatment of the chronic cutaneous ulcers more effective and less inconvenient and, in particular, to overcome the significant limits imposed by the known (surgical and non-surgical) debridement methods.

In addition to what has been highlighted above with specific reference to the problem of the chronic cutaneous ulcers, it should be observed that the phenomena of microbial proliferation are further responsible for, or involved in, pathologies relating to the oral cavity, such as the periodontal disease and the perimplantitis.

The term "periodontal disease" defines a group of inflammatory pathologies that attack the system of tooth supporting tissues or periodontium, which can be distinguished in superficial periodontium (gingiva) and deep periodontium (periodontal ligament, root cementum and alveolar bone). The most frequent cause of periodontal disease is microbial, in particular bacterial, and the microorganisms involved are those normally present in the bacterial plaque. The infection occurs when—due to an excessive bacterial proliferation and/or a reduction of the organism's defensive mechanisms—the normal equilibrium is lost that keeps the tissues healthy. When the inflammation involves only the superficial periodontium the clinical picture is gingivitis, when on the other hand (in the absence of a suitable treatment) the inflammation extends beyond the gingival region, affecting the deep zones (alveolar bone, periodontal ligament and cement) of the periodontium, the clinical picture is periodontitis. Gingivitis attacks the gingiva near the tooth (marginal gingiva) and the symptoms (which are completely reversible after suitable therapeutic treatment) comprise reddening of the gingival margin, oedema and bleeding following mechanical stimulation. In the periodontitises the tooth supporting system is destroyed and it is manifested by attachment and bone loss, formation of pockets and shrinkage of the gingiva. The typical sign of the periodontitises is the formation of a periodontal pocket associated with dental looseness. The destruction of the teeth supporting tissues is in most cases irreversible. The periodontitis is always preceded by gingivitis and so by preventing gingivitis it is possible to prevent the periodontitis.

Gingivitises and periodontitises are pathologies that show an essentially bacterial but multifactorial aetiology, in which three cofactors interact: susceptibility of the host, environmental factors and behavioural factors. The bacterial plaque, although being necessary to the onset of the periodontal disease, is influenced by the interaction with the host and by numerous local and systemic factors, such as for example diabetes, which affect the clinical course. In Italy, the periodontal disease affects about 60% of the population and the individuals between 35 and 44 years of age are particularly affected. This percentage includes both the surface form (gingivitis, which affects the portion of gingiva near the tooth or marginal gingiva) and the deep form (periodontitis proper).

The treatment of the periodontal disease has to aim to stop the progression of the disease and prevent or reduce the onset of possible recurrences. In particular, the periodontitis therapy has to take into account the multifactorial nature of the pathology and provide clinical treatments that are able to face the complexity of the problem. The control of the causal agents is pursued and achieved through the mechanical removal (for example, by curettes or ultrasound devices) of the supragingival and subgingival bacterial plaque, as well as through the possible use of topical or systemic drugs. Among the periodontal pathogenic microorganisms the following species are counted: *Aggregatibacter actinomycetemcomitans, Porphyromonas gingivalis, Tannerella forsythia* and *Treponema denticola*.

From what has been highlighted above, it is clear that in order to oppose effectively the periodontal disease, it is necessary to reduce the bacterial load in the oral cavity.

The term "perimplantitis" defines an inflammatory process that attacks the tissues adjacent to an osseointegrated implant (artificial root that acts as a support for a fixed dental prosthesis) and leads to a destruction and loss of alveolar bone tissue. The causes are variable and may relate both to the surgical procedure of implanting the prosthesis and to the accompanying bacterial infections. It should nevertheless be noted that the bacterial aetiological component aggravates the problems connected to the surgical implant of the prosthesis. In order to safeguard the osseointegration process, the administration of antibiotic and anti-inflammatory drugs, a possible surgical treatment (so-called curettage) of the concerned area, as well as the guided bone regeneration, are used.

All the treatments aim to eliminate the bacteria from the surface of the implant, both blind technique (i.e. without piercing the visible gingiva) and open surgery (i.e. piercing and raising the gingiva). The blind technique treatments are less invasive but have cannot be associated with the bone regeneration, which always requires lifting of a gingiva flap. Furthermore, they are treatments that are conducted in a substantially "blind" manner, which do not enable to view and check whether the microbial load in the treated areas has actually been minimized.

The treatments of mechanical type provide for the use of curettes, sodium bicarbonate jet devices or powder jet devices, milling machine (for removing all the surface coils and roughnesses of the implant). The non-mechanical treatments provide for the use of antiseptic and antibiotic solutions, both as mouthwashes and as compositions that release active principles slowly. The laser can be used to sterilize the surfaces physically.

A drawback of all the treatments that limit themselves to eliminating the bacteria by disinfecting chemically or sterilizing physically is that the bacteria will again colonize the disinfected or sterilized zones. This is because the bacteria are not only on the implants but are substantially ubiquitous in the oral cavity.

It should also be noted that, both in the perimplantitises and in the periodontal disease of medium to severe degree, it is often necessary to accomplish a surgical therapy (debridement under local anaesthesia) to remove the infected tissue adjacent to the implant or to the tooth. Nevertheless, the surgical procedure alone is not able to remove the biofilm completely that forms in the lesion, so that it is necessary to associate the administration of antibiotics and disinfectants with the debridement.

In the context of the pathologies of the oral cavity aphthae have also to be mentioned, because of the particular frequency thereof.

The term "aphtha" defines a painful ulcer caused by a breakage of the mucosa inside the oral cavity. These ulcers form periodically and can heal completely between one episode and the next. In most cases, the individual aphthae have a duration varying between 8 and 10 days. Most of aphthae appear on the surfaces of the non-keratinized epithelia of the mouth and, more specifically, everywhere except for adherent gingiva, hard palate and back of the tongue. The symptoms of the aphthae vary from a mild discomfort up to difficulty in eating and drinking. The condition is very common and affects about 20% of the population. The formation of aphthae has often infantile or adolescent onset and the condition usually lasts several years before gradually disappearing. Currently no definitive treatment has yet been identified for the aphtha and the treatment focuses on pain management, on the reduction of the healing times and on the reduction of the frequency of recurrences.

From what has been disclosed above, it is clear that the optimum treatment of skin pathologies (chronic cutaneous ulcers) and pathologies of the oral cavity (periodontal disease, perimplantitis, aphtha) requires a drastic reduction of bacterial contamination, which in turn requires an effective removal of the biofilm and of the necrotic or infected tissues. Nevertheless, the most used surgical method for removing necrotic or infected tissues, i.e. the debridement, has numerous drawbacks (risk of bleeding for the patient, need for hospitalization, complexity and high costs of execution).

Therefore, a strong need is felt for new compositions that enable the biofilm and the necrotic or infected tissues to be removed effectively that are present in the chronic cutaneous ulcers, in the periodontal or peri-implant pockets and in the wounds of the mucosa in general (for example, aphthae of the oral cavity).

OBJECTS OF THE INVENTION

An object of the invention is to improve the known procedures for removing the biofilm as well as the necrotic or infected tissues present in the skin lesions, in particular in the chronic cutaneous ulcers, and in the mucosal lesions, in particular in the mucosal lesions of the oral cavity.

Another object is to provide compositions that are usable for removing the biofilm and the necrotic or infected tissues present in the chronic cutaneous ulcers, in the periodontal or peri-implant pockets and in the mucosal wounds of the oral cavity, such as for example aphthae.

A further object is to provide compositions that can be applied in simple manner to chronic cutaneous ulcers, periodontal or peri-implant pockets and wounds of the mucosa of the oral cavity and enable the biofilm and the necrotic or infected tissues to be removed in rapid manner.

SHORT DESCRIPTION OF THE INVENTION

According to the invention, a composition as defined in claim 1 is provided, which is usable for removing a biofilm and necrotic or infected tissues from skin lesions and lesions of the oral cavity.

The composition according to the invention enables the previously mentioned objects to be achieved. In fact, the Inventors have discovered and verified experimentally that a chemical composition containing a strongly hydrophilic substance is able to perform a strongly dehydrating action on the bottom of a chronic cutaneous ulcer, on a periodontal or peri-implant pocket or on a generic mucosal lesion of the oral cavity, such as for example an aphtha. The aforesaid dehydrating action produces a plurality of effects, namely the denaturation of the inflammatory proteins, the drying and the detachment of necrotic biological tissues and above all the elimination of microorganisms, in particular bacteria and fungi.

The composition according to the invention comprises methanesulfonic acid as an active principle, in combination with suitable coformulants (chemically inert substances) that are able to adjust, in particular attenuate, the acidity of the composition. The composition according to the invention is able to remove the biofilm and necrotic tissues from infected zones of the skin or mucosa of the oral cavity within a few tens of seconds from the application. The composition can be applied directly on the zone to be treated (chronic cutaneous ulcer, periodontal or peri-implant pocket, aphtha) with any means that is suitable for permitting the distribution thereof. After a contact time of a few tens of seconds has elapsed, the composition can be easily removed from the skin or from the mucosa through the use of a simple gauze or by washing the treated skin or mucosa surface with physiological solution or with a flow of sterile water (removable by suction in the case of treatment performed inside the oral cavity).

Therefore, by applying the composition according to the invention on a skin lesion or on a lesion of the mucosa of the oral cavity it is possible to obtain the same effects that are obtainable through a surgical debridement, without however the well-known drawbacks connected with the latter procedure. This new and effective therapeutic possibility is usable, with significant benefit for the patient, in cases of slight, medium and high seriousness.

SHORT DESCRIPTION OF THE DRAWINGS

The invention can be better understood and implemented with reference to the enclosed drawings that illustrate an embodiment thereof by way of non-limiting example in which.

DETAILED DESCRIPTION OF THE INVENTION

Figure 1:
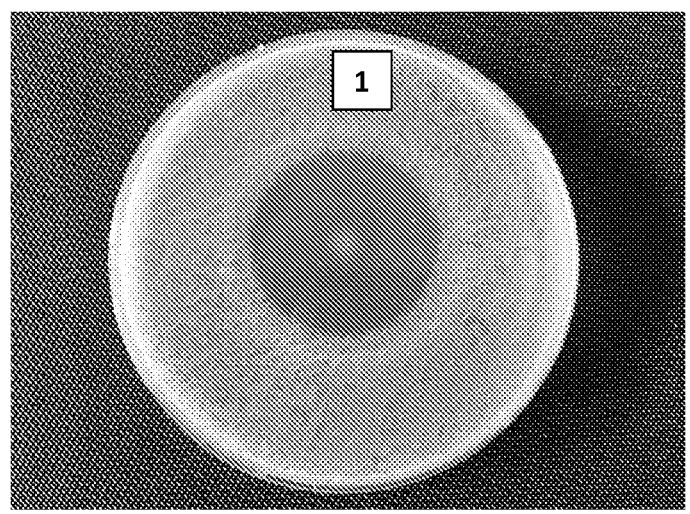
FIG. 1 is a photograph of a Petri dish showing a microbial growth inhibition halo around the depositing zone of a sample of an embodiment of the composition according to the invention.

The composition according to the invention, comprising methanesulfonic acid, can be formulated as a solution, gel or cream and can be easily applied on chronic cutaneous ulcers or on lesions of the mucosa of the oral cavity, such as for example periodontal pockets, perimplantitises or aphthae. A surprisingly unexpected property of the composition according to the invention is that the latter is able to act on the biofilm and on the necrotic or infected tissues, causing a rapid desiccation thereof and enabling the removal thereof (through washing or sterile gauze) only a few seconds after the application and thus avoiding complicated, painful and costly surgical procedures (debridement).

The action of the composition is due to the release of hydrogen ions ($H^+$) or protons that, possessing a great hydration enthalpy (−1130 KJ/mole), cause the dehydration of the microbial species that make up the biofilm or proliferate in the infected tissues. This action mechanism is achieved regardless of the microbial species present and makes the composition according to the invention active against any microbial species, whether bacterial, fungal or viral.

The Inventors have carried out researches to identify the most suitable source of protons, namely a source that is such as to enable an effective release of the protons in contact with the skin or the mucosa of the oral cavity, with resulting denaturation of the microbial proteins present therein, without however causing damages to the healthy tissue surrounding the lesions. This requires the preparation of appropriate formulations where the release of the protons is optimized, for example by varying the degree of viscosity of the formulations on the basis of the type of lesion for which the use of the composition according to the invention is intended.

The potentially usable sources of protons essentially consist of strong acids (HA), which have to be used in concentrated form, namely in the presence of the least possible amount of water. This is required because the dissociation of the strong acid into $H^+$ protons and $A^-$ anions has to occur in contact with the microbial species, subtracting molecules of water from the latter, which molecules will form the hydration sphere of the H+ protons with release of thermal energy (~1130 KJ/mole). The dosage of the H+ protons released by the acid species in concentrated form is problematic as it is not possible to dilute with water, which nevertheless represents the best solvent for solubilizing methanesulfonic acid.

As it is known, the acid dissociation constant ($K_a$) relating to the reaction HA →$H^+$+$A^-$ is defined by the following relation:

$$K_a=[H^+][A^-]/[HA]$$

in which the concentrations in moles/litre of the different species are indicated between square brackets. The negative decimal logarithm of the acid dissociation constant is defined as $pK_a$ ($pK_a$=-log $K_a$).

In the following Table 1, the $pK_a$ values are shown (at a temperature of 25° C.) of the main strong acids, which dissociate completely, or almost completely, in an aqueous environment. From Table 1 it can be inferred that the trifluoromethanesulfonic acid is the strongest acid (namely, the acid having the highest $pK_a$ value), whereas the trifluoroacetic acid is the weakest acid:

TABLE 1

| Acid | Chemical formula | $pK_a$ |
|---|---|---|
| Trifluoromethanesulfonic | $CF_3SO_3H$ | −13 |
| Hydroiodic | HI | −10 |
| Perchloric | $HClO4$ | −10 |
| Hydrobromic | HBr | −9 |
| Hydrochloric | HCl | −8 |
| Sulphuric | $H_2SO_4$ | −3 |
| Nitric | $HNO_3$ | −1.4 |
| Methanesulfonic | CH3SO3H | −1.2 |
| Trifluoroacetic | CF3COOH | −0.25 |

Considering the volatility of the hydroiodic, hydrobromic, hydrochloric and trifluoroacetic acids, as well as the oxidizing action of the perchloric and nitric acids, which can cause undesired effects on the skin and on the mucosa of the oral cavity, the Inventors focused the attention on the sulphuric and on the methanesulfonic acid and deemed the use of the latter to be preferable. In fact, the methanesulfonic acid (MSA) has a dissociation constant that is about sixty times less than that of the sulphuric acid, which makes the methanesulfonic acid substantially more suitable for use on the skin and in the oral cavity. The methanesulfonic acid is a stable strong acid and a key intermediate in the biogeochemical cycle of the sulphur. The methanesulfonic acid is formed in great quantities in the atmosphere by the chemical oxidation of the atmospheric dimethyl sulphide (DMS) (most of which is of organogenic origin) and is deposited on the earth through rain, snow as well as dry deposition. Therefore, this acid is usually defined as a "green acid" (M. D. Gernon, M. Wu, T. Buszta, P. Janney, Green Chem. 1 (1999) 127-140; S. C. Baker, D. P. Kelly, J. C. Murrell, Nature 350 (1991) 627-628.). The methanesulfonic acid has a low tendency to oxidize organic compounds and a high thermal stability, which makes it usable in liquid form over a wide range of temperatures. The methanesulfonic acid is odourless, due to the very low vapour tension, and does not produce hazardous volatile substances, which enables a safe handling thereof. Furthermore, the methanesulfonic acid is provided with a greater penetration capacity against the biofilm.

The Inventors further provided for the use of the methanesulfonic acid in combination with small quantities of suitable proton acceptors (or protonic acceptors), which enable the acidity of the composition according to the invention to be adjusted, and more exactly to be reduced. The protonic concentration has to be reduced because the protons, if they are released in an excessive quantity, may cause the dehydration of the epithelial cells with consequent oedema, erythema, desquamation and tissue necrosis with formation of ulcers. By reducing the concentration of the protons released by the methanesulfonic acid, the latter can be effectively used in the treatment of lesions (chronic cutaneous ulcers, periodontal disease, perimplantitises and aphthae) in which the biofilm is present for producing a desired dehydrating effect against the contaminating microbial species without however damaging the surrounding healthy tissues.

In one embodiment of the composition according to the invention—defined below as "first formulation"—the proton acceptor comprises a weak acid salt that is soluble in the concentrated methanesulfonic acid. The anion of the weak acid, by capturing part of the protons released by the methanesulfonic acid, avoids irritative phenomena, at the same time enabling the dehydration effect to be maintained. This enables any microbial species to be deactivated aspecifically that is responsible for skin, gingival or periodontal infections or aphtha.

In the following Table 2, the dissociation constants are shown of a plurality of weak acids, the anions of which (contained in the corresponding salts that are soluble in methanesulfonic acid) can be suitably used:

TABLE 2

| Acid | Formula | $K_{a1}$ | $K_{a2}$ | $K_{a3}$ |
|---|---|---|---|---|
| Acetic | $CH_3COOH$ | $1.74 \times 10^{-5}$ | | |
| Ammonium ion | $NH_4^+$ | $5.70 \times 10^{-10}$ | | |
| Anilinium ion | $C_6H_5NH_3^+$ | $2.50 \times 10^{-5}$ | | |

TABLE 2-continued

| Acid | Formula | $K_{a1}$ | $K_{a2}$ | $K_{a3}$ |
|---|---|---|---|---|
| Boric | $H_3BO_3$ | $5.81 \times 10^{-10}$ | | |
| Carbonic | $H_2CO_3$ | $4.44 \times 10^{-7}$ | $4.69 \times 10^{-11}$ | |
| Citric | $HOOC(OH)C(CH_2COOH)_2$ | $7.45 \times 10^{-4}$ | $1.73 \times 10^{-5}$ | $4.02 \times 10^{-7}$ |
| Ethylenediamine-tetraacetic | $[(HOOC)_2CH_2NCH_2]_2$ | $10^{-2}$ | $2 \times 10^{-3}$ | $7 \times 10^{-7}$; $K_{a4}, 5 \times 10^{-11}$ |
| Phosphoric | $H_3PO_4$ | $7.11 \times 10^{-3}$ | $6.32 \times 10^{-8}$ | $4.5 \times 10^{-13}$ |
| Phosphorous | $H_3PO_3$ | $3 \times 10^{-2}$ | $1.62 \times 10^{-7}$ | |
| Formic | HCOOH | $1.80 \times 10^{-4}$ | | |
| Glycolic | $HOCH_2COOH$ | $1.47 \times 10^{-4}$ | | |
| Gluconic | $HOOC(CH_2OH)_4CH_2OH$ | $7.4 \times 10^{-3}$ | | |
| Hydrazinium ion | $H_2NNH_3^+$ | $1.05 \times 10^{-8}$ | | |
| Hydrazoic | $HN_3$ | $2.2 \times 10^{-5}$ | | |
| Hypochlorous | HClO | $3.0 \times 10^{-8}$ | | |
| Lactic | $CH_3CHOHCOOH$ | $1.39 \times 10^{-4}$ | | |
| Malic | $HOOCCHOHCH_2COOH$ | $3.48 \times 10^{-4}$ | $8.00 \times 10^{-6}$ | |
| Mandelic | $C_6H_5CHOHCOOH$ | $4.0 \times 10^{-4}$ | | |
| Methylammonium ion | $CH_3NH_3^+$ | $2.3 \times 10^{-11}$ | | |
| Succinic | $HOOCCH_2CH_2COOH$ | $6.21 \times 10^{-5}$ | $2.31 \times 10^{-6}$ | |
| Tartaric | $HOOC(CHOH)_2COOH$ | $9.20 \times 10^{-4}$ | $4.31 \times 10^{-5}$ | |

Given the low $K_a$ values, the anions of the weak acids listed in Table 1 (appropriately incorporated into suitable salts) can sequester part of the protons of the methanesulfonic acid.

In another embodiment of the composition according to the invention—defined below as "second formulation"—the proton acceptor further comprises silicon dioxide particles, which can be pretreated with an ammonium hydroxide ($NH_4OH$) solution and subsequently subjected to anhydrification through heat treatment at 100° C. to increase the neutralizing efficacy thereof. The second formulation can be considered to be substantially complementary to the first formulation.

In a further embodiment of the composition according to the invention—defined below as "third formulation"—the proton acceptor comprises tetraethoxysilane, which acts as a cross-linking agent as well as a sequestering agent against the protons of the methanesulfonic acid. The third formulation can be substantially complementary to the first and to the second formulation.

In another further embodiment of the composition according to the invention—defined below as "fourth formulation"—the proton acceptor comprises anhydrous dimethyl sulfoxide (DMSO), which is added to a concentrated solution of methanesulfonic acid. The DMSO enables the acidity to be reduced of the composition according to the invention by protonation of the oxygen atom thereof. The fourth formulation can be substantially complementary to the first, to the second and to the third formulation.

In a further other embodiment of the composition according to the invention—defined below as "fifth formulation"—the proton acceptor comprises polyethylene glycol. This enables the acidity of the composition according to the invention to be reduced through the protonation of the oxygen present in the chain of the polymers, as well as the viscosity of the composition according to the invention to be increased. The fifth formulation can be substantially complementary to the first, to the second, to the third and to the fourth formulation.

In a still further embodiment of the composition according to the invention—defined below as "sixth formulation"—the proton acceptor comprises molecular species containing amine groups, or more in general nitrogen atoms, which can bind protons.

The various embodiments of the composition disclosed above enable an equilibrium to be established between the methanesulfonic acid (indicated by HA) and proton acceptors (indicated generally by B). This equilibrium is disclosed by the reaction $HA^+ B \leftrightarrow A^- + HB$ and has as a result a reduction of the concentration of methanesulfonic acid without massive introduction of dilution water, maintaining the antimicrobial effect of the composition according to the invention and the efficacy of the latter in removing biofilm and tissues rapidly and painlessly.

The chemical components that are more suitable for preparing the various embodiments of the composition according to the invention are listed below. Of these, the methanesulfonic acid is the active principle, whilst all the other listed components are suitable proton acceptors:

Methanesulfonic acid 99.0%; CAS N.75-75-2

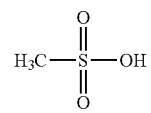

Anhydrous sodium carbonate or $Na_2CO_3$; CAS N. 497-19-8

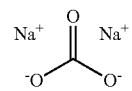

5-amino-2-mercaptobenzimidazole; CAS N. 2818-66-8

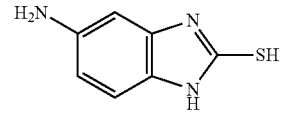 [SMILES: Nc1ccc2[nH]c(S)nc2c1]

Ethylenediaminetetraacetic acid tetrasodium salt or EDTANa4; CAS N. 13235-34-4

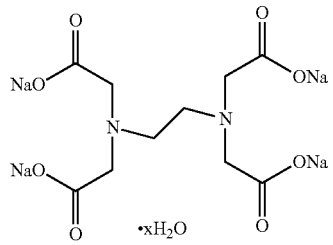

Sodium gluconate; CAS N. 527-07-1

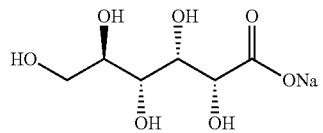

Sodium tartrate dihydrate; CAS N. 6106-24-7

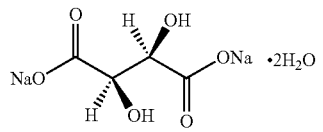

2-mercapto-5-benzimidazole sodium sulfonate; CAS N. 207511-11-3

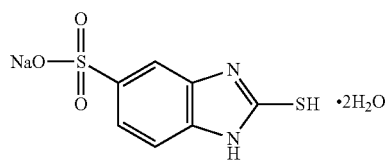

Dimethyl sulfoxide or DMSO or $(CH_3)_2SO$, CAS N. 67-68-5

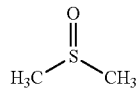

Polyethylene glycol 400 or PEG 400 (average molecular weight: 400 Da), CAS. 25322-68-3; polyethylene glycol 600 or PEG 600 (average molecular weight: 600 Da), CAS 9004-74-4

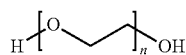

Silicon dioxide or $SiO_2$; CAS 112945-52-5
Tetraethyl orthosilicate or tetraethoxysilane or TEOS or $Si(OC_2H_5)_4$; CAS N. 78-10-4

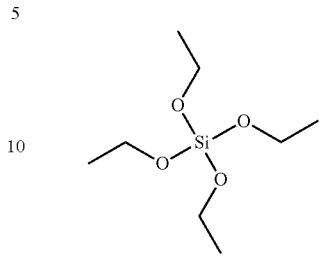

In the following Tables 3-8, possible qualitative and quantitative compositions of the first, second, third, fourth, fifth and sixth formulation of the composition according to the invention are disclosed in greater detail by way of non-limiting example. The expression "possible qualitative and quantitative compositions" should be understood in the sense that a person skilled in the art can easily and suitably modify each of the formulations of the composition according to the invention (for example, through the addition of pharmacologically acceptable excipients) on the basis of the physical form of administration (solution, cream or gel), provided that the composition always contains methanesulfonic acid as an active principle and at least one suitable proton acceptor.

Tables 3-8 disclose the qualitative and quantitative composition of six liquid (solution) or gel embodiments of the composition according to the invention:

TABLE 3

First formulation

| Component | Percentage by weight |
|---|---|
| Methanesulfonic acid | 70-90% |
| Sodium carbonate | 0.5-2% |
| 5-amino-2-mercaptobenzimidazole | 1-2% |
| EDTANa4 | 1-6% |
| Sodium gluconate | 1-6% |
| Sodium tartrate dihydrate | 2-6% |
| 2-mercapto-5-benzimidazole sodium sulfonate | 1-4% |

TABLE 4

Second formulation

| Component | Percentage by weight |
|---|---|
| Methanesulfonic acid | 70-90% |
| 5-amino-2-mercaptobenzimidazole | 1-2% |
| EDTANa4 | 1-6% |
| Sodium gluconate | 1-6% |
| Sodium tartrate dihydrate | 2-6% |
| 2-mercapto-5-benzimidazole sodium sulfonate | 1-4% |
| $SiO_2$ | 0.1-7% |

TABLE 5

Third formulation

| Component | Percentage by weight |
|---|---|
| Methanesulfonic acid | 70-90% |
| 5-amino-2-mercaptobenzimidazole | 1-2% |

TABLE 5-continued

Third formulation

| Component | Percentage by weight |
|---|---|
| EDTANa4 | 1-6% |
| Sodium gluconate | 1-6% |
| Sodium tartrate dihydrate | 2-6% |
| 2-mercapto-5-benzimidazole sodium sulfonate | 1-4% |
| $SiO_2$ | 0.1-7% |
| TEOS | 0.1-2% |

TABLE 6

Fourth formulation

| Component | Percentage by weight |
|---|---|
| Methanesulfonic acid | 70-90% |
| Dimethyl sulfoxide | 10-30% |
| $SiO_2$ | 0.1-7% |
| TEOS | 0.1-2% |

TABLE 7

Fifth formulation

| Component | Percentage by weight |
|---|---|
| Methanesulfonic acid | 70-90% |
| Sodium gluconate | 1-6% |
| Sodium tartrate dihydrate | 2-6% |
| $SiO_2$ | 0.1-7% |
| TEOS | 0.1-2% |
| PEG 400 or PEG 600 | 1-10% |

TABLE 8

Sixth formulation

| Component | Percentage by weight |
|---|---|
| Methanesulfonic acid | 70-90% |
| 5-amino-2-mercaptobenzimidazole | 1-8% |
| EDTANa4 | 1-8% |
| 2-mercapto-5-benzimidazole sodium sulfonate | 1-8% |

The procedure for preparing the six formulations referred to in the previous Tables 3-8 is not disclosed in detail below, because the chemical components of the various formulations can be added to the methanesulfonic acid according to a variable order and nevertheless without altering the properties of the final solution. In fact, the different chemical components are solubilized without reactions intervening that are able to interfere with the phenomenon of the protonation of the proton acceptors.

By way of non-limiting example of the invention, two tests of in vitro and in vivo antimicrobial activity of the composition according to the invention (Example 1; Example 2) and two procedures for treating lesions (skin lesions and lesions of the mucosa of the oral cavity) that are based on the use of the composition according to the invention (Example 3; Example 4) are disclosed below.

Example 1—Test of In Vitro Antimicrobial Activity

The antimicrobial activity of the first, second, third, fourth, fifth and sixth formulation of the composition according to the invention was tested against the following strains of microorganisms (purchased from Diagnostic International Distribution S.p.A.): *Pseudomonas aeruginosa* ATCC 15442, *Staphylococcus aureus* ATCC 6538, *Escherichia coli* ATCC 10536, *Enterococcus hirae* ATCC 10541, *Candida albicans* ATCC 10231. Mixtures of the different strains of microorganisms were prepared, having concentrations expressed as colony forming units (CFU) comprised between $1.5 \times 10^{12}$–$5.5 \times 10^{12}$ for each species. 100 µl samples of the mixture were inoculated on Petri dishes containing TSA (Tryptone Soya Agar) solid culture medium. The inoculation was carried out according to a known and standardized analytical method, namely by depositing the liquid sample on the surface of the agar by a micropipette and distributing the liquid sample on the surface of the agar by using sterile glass beads. Subsequently, 50 µl aliquots of the six formulations of the composition according to the invention were deposited in a central zone of the agar of each Petri dish. The dishes were then incubated at 37° C. for 24 h.

Figure 2:
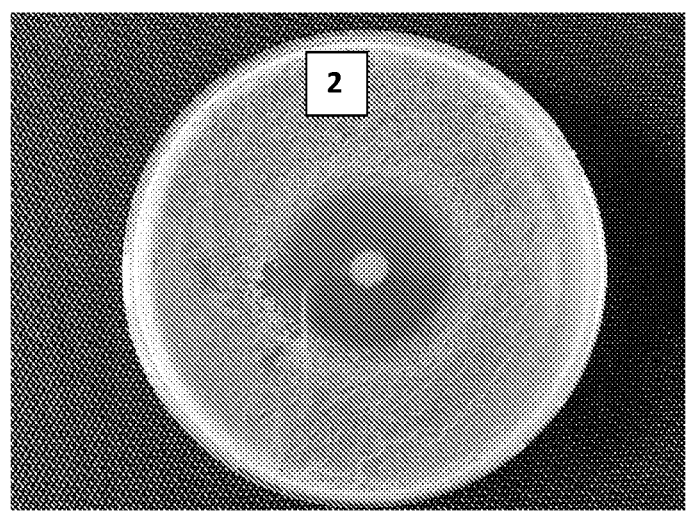
FIG. 2 is a photograph of a Petri dish showing a microbial growth inhibition halo around the depositing zone of a sample of another embodiment of the composition according to the invention.
Figure 3:
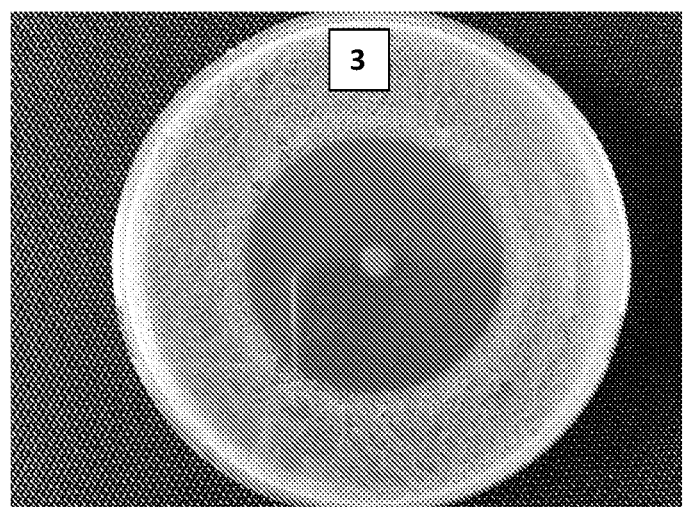
FIG. 3 is a photograph of a Petri dish showing a microbial growth inhibition halo around the depositing zone of a sample of a further embodiment of the composition according to the invention.
Figure 4:
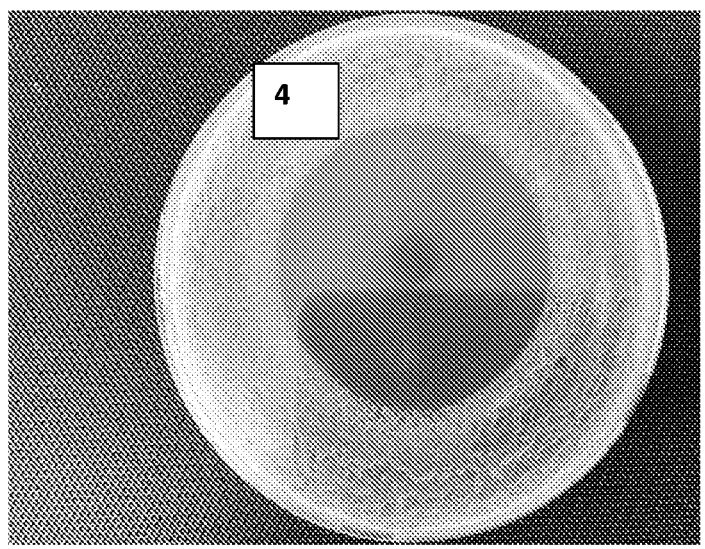
FIG. 4 is a photograph of a Petri dish showing a microbial growth inhibition halo around the depositing zone of a sample of another further embodiment of the composition according to the invention.
Figure 5:
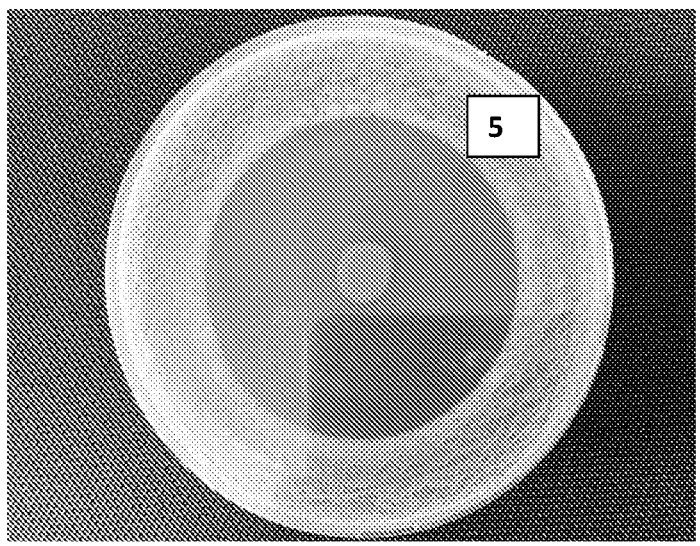
FIG. 5 is a photograph of a Petri dish showing a microbial growth inhibition halo around the depositing zone of a sample of a further other embodiment of the composition according to the invention.
Figure 6:
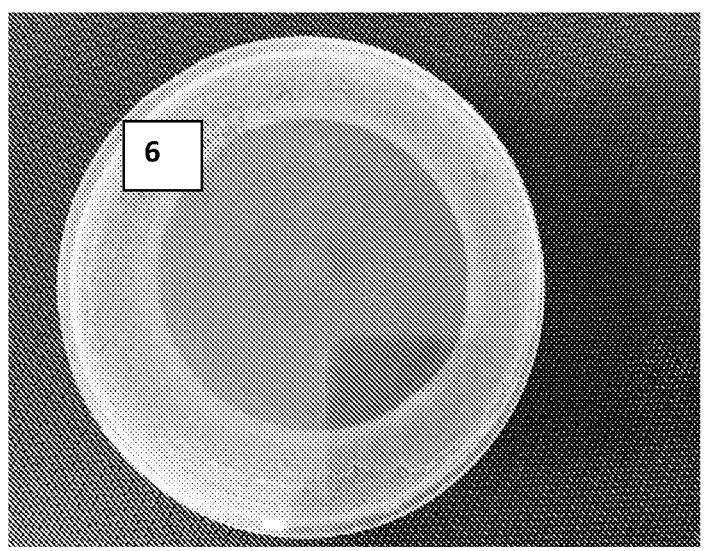
FIG. 6 is a photograph of a Petri dish showing a microbial growth inhibition halo around the depositing zone of a sample of a still further embodiment of the composition according to the invention.

FIGS. 1 to 6 show six Petri dishes marked 1 to 6, in each of which a 50 µl aliquot was deposited respectively of the first, second, third, fourth, fifth and sixth formulation of the composition according to the invention.

After the incubation, the dishes were examined in order to evaluate the microbial proliferation (formation of colonies) and the width of the inhibition halo (namely, the width of the portion of medium in which the microbial proliferation had been inhibited) surrounding the zone of agar on which samples of the six formulations had been deposited. As shown in FIGS. 1-6, in all the Petri dishes clear zones of microbial growth inhibition were observed, surrounding the depositing zones of the preparations according to the invention. The analytical result obtained indicates that the six different formulations of the composition according to the invention are able to inhibit the growth of $10^{11}$ CFU of gram-positive bacteria, gram-negative bacteria and of the fungal species *Candida albicans*.

Example 2—Test of In Vivo Antimicrobial Activity

The in vivo antimicrobial activity of the composition according to the invention was tested, which composition was prepared in the form of a gel according to the fourth formulation, in which the methanesulfonic acid is supported on silicon. Six volunteers, namely (six) patients diagnosed with chronic periodontal disease (periodontitis) were selected randomly. The selected patients were of an age comprised between 35 and 55 years and had not previously received any surgical or non-surgical periodontal therapy. None of the aforesaid patents was pregnant, had taken antibiotics, had used antibacterial mouthwash in the six previous months, had teeth with furcation involvement or had a story of abuse of alcohol or drug. Before any treatment, at the initial time (day) T1, each of the six patients was subjected to a subgingival microbiological sampling through the use of four sterile paper tips (of the type used to dry the endodontic canals), which were inserted into the periodontal pockets in four quadrants (right maxillary quadrant, left maxillary quadrant, right mandibular quadrant, left mandibular quadrant) and left therein for 20 seconds. The insertion site of each paper tip was isolated by using cylindrical cotton swabs. The gel containing the composition according to the invention was applied with a small brush in each periodontal pocket and left therein for a period of 15 seconds. After this time elapsed, the gel was removed by washing abundantly with physiological solution for 30 seconds and simultaneously sucking the liquid.

After the aforesaid procedure had been completed and subject to drying with a jet of air, a second subgingival microbiological sampling was carried out (by using sterile paper tips), at the time T2, in the same periodontal pockets examined at the initial time T1. The second subgingival microbiological sampling was carried out through the same procedure used in the initial time T1. The paper tips used for each patient at the time T1 and at the time T2 were transferred in sterile test tubes and sent to a microbiological laboratory, for subsequent extraction of the DNA and PCR analysis (polymerase chain reaction). The bacterial count through PCR was directed mainly to *Tannerella forsythia* (TF), *Treponema denticola* (TD), *Fusobacterium nucleatum* (FN) and *Campylobacter rectus* (CR), which are the bacterial species that are more implicated in the periodontitis. The total bacterial load (TBL) was also determined through PCR.

In the PCR analysis, the primers and the oligonucleotide probes were based on gene sequences of 16S rRNA of the human oral microbiome database (HOMD 16S rRNA RefSeq Version 10.1), which counts 845 items. Absolute quantification assays were carried out through PCR by using the 7500 Sequence Detection System (Applied Biosystems). The amplification profile was started with an incubation period of 10 min at 95° C. to activate polymerase, followed by an amplification in two steps of 15 sec to 95° C. and 60 sec at 57° C. for 40 cycles. All these steps were carried out by including controls without amplification probes to exclude the contamination of the reagents. Plasmides containing specific DNA sequences (purchased from Eurofins MWG Operon, Ebersberg, Germany) were used for the quantitative evaluation. These positive controls were used to plot standard curves (by showing in Cartesian axes the threshold cycle values against the logarithm of the number of copies), which were used to check the amplification efficiency and for the quantification of targets in each sample (J Biol Regul Homeost Agents, 2017, 31(1): 257-262; J Biol. Regul. Homeost. Agents, 2016, 30 (2 Suppl 1): 87-97; J Biol Regul Homeost Agents, 2015, 29(3 Suppl 1): 101-10.).

The absolute quantities of different bacterial species in periodontal pockets of patients affected by periodontitis, detected through bacterial count at the initial time T1 and at the time T2, are shown in the following Table 9:

TABLE 9

| TF 1 | TF 2 | TD 1 | TD 2 | FN 1 | FN 2 | CR 1 | CR 2 | TBL 1 | TBL 2 |
|------|------|------|------|------|------|------|------|-------|-------|
| 357  | 0    | 1205 | 0    | 126485 | 1970 | 1678 | 0    | 645280 | 54501 |
| 181  | 0    | 327  | 0    | 22031 | 1561 | 1049 | 92   | 162489 | 63541 |
| 9177 | 0    | 10059 | 0   | 739463 | 823 | 51446 | 0    | 4430648 | 52805 |
| 400  | 185  | 537  | 202  | 82289 | 24180 | 3211 | 844  | 315053 | 110991 |
| 69   | 0    | 210  | 63   | 137127 | 28550 | 11395 | 3575 | 979525 | 302285 |
| 0    | 0    | 0    | 0    | 16985 | 4887 | 2104 | 119  | 186067 | 62545 |

(1: initial sampling; 2: post-treatment sampling; TF: *Tannerella forsythia*; TD: *Treponema denticola*; FN: *Fusobacterium nucleatum*; CR: *Campylobacter rectus*; TBL: total bacterial load).

The results of the microbiological analysis were treated statistically, in particular by carrying out a related-samples Wilcoxon non-parametric test by SPSS software. The Wilcoxon test demonstrated a statistically significant reduction ($p \leq 0.05$) of the quantity of each bacterial species after the local treatment with the gel containing the composition according to the invention. The results of the Wilcoxon test are shown in the following Table 10:

TABLE 10

| Null hypothesis | Sig | Decision |
|---|---|---|
| The median of the differences between TF1 and TF2 is equal to 0 | 0.018 | Rejects null hypothesis |
| The median of the differences between TD1 and TD2 is equal to 0 | 0.018 | Rejects null hypothesis |
| The median of the differences between FN1 and FN2 is equal to 0 | 0.012 | Rejects null hypothesis |
| The median of the differences between CR1 and CR2 is equal to 0 | 0.012 | Rejects null hypothesis |
| The median of the differences between TBL1 and TBL2 is equal to 0 | 0.012 | Rejects null hypothesis |

It should be further noted that no (immediate or after a lapse of time) side effects or adverse reactions were observed after the local application of the gel containing the composition according to the invention. In fact, the patients reported no sensations of pain, burning, tingling and/or numbness during the entire period of treatment.

Example 3—Treatment of Patients Affected by Chronic Cutaneous Ulcers

The composition according to the invention was tested on over 20 patients who were volunteers, by applying a treatment protocol comprising the following steps:
Removing with a sterile gauze the easily removable necrotic materials that are present on the bottom of the ulcer;
Drying completely the bottom of the ulcer;
Only in the case of particularly sensitive patients, for whom a painful response is expected, pre-treating the bottom of the ulcer for a time of about 5 minutes with a pack of ointment containing 5% lidocaine;
Removing the pack, washing the ulcer to remove the lidocaine ointment and drying;
Applying the composition according to the invention on the bottom of the ulcer and on the surrounding skin for about 1 cm beyond the edge of the ulcer, by using the finger of a hand covered by sterile single-use glove;
Letting the composition according to the invention to act for about 20-30 seconds;
Washing abundantly with sterile physiological solution;
Drying with sterile gauze;
Rubbing the bottom of the ulcer with sterile gauze to remove the desiccated material;
Leaving on the bottom of the ulcer the possible desiccated material that did not detach itself through the effect of rubbing with the gauze;

Covering the ulcer with a sterile greasy gauze or with another type of suitable medication (according to the choice of the operator);

Bandaging the zone according to known procedure;

Performing subsequent checks at 7-day intervals, or at shorter intervals if deemed necessary.

During each check, the aforesaid protocol provides for proceeding in the following manner:

Removing bandages and medication;

Removing progressively, by using normal pliers and scissors and starting from the edges of the lesion, the desiccated material left on the bottom of the ulcer;

Covering the ulcer with a sterile greasy gauze or with another type of suitable medication (according to the choice of the operator);

Bandaging the zone according to known procedure.

When the bottom of the ulcer is covered by granulation tissue, upon complete granulation and according to the choice of the operator, it is possible to graft skin and/or skin substitute in the lesion to complete the healing process.

The treatment protocol disclosed above resulted to be effective in desiccating the bottom of the ulcers in all the treated patients. No complications and/or side effects emerged at the systemic or local level or on the perilesional skin. In all the treated patients the residual desiccated material disappeared progressively at the end of the procedure without the need for an additional intervention and left a granulation tissue on the bottom of the lesion.

Therefore, the application of the composition according to the invention (containing methanesulfonic acid together with proton acceptors) produced in all the cases a complete restoration of the tissues in the lesion, promoting the healing thereof. The treatment protocol disclosed above can be applied to all the patients, thus avoiding complicated, costly and potentially risky surgical procedures. Furthermore, the treatment with the composition according to the invention can reduce the need to use antibiotic therapies, which are substantially costly and associated with the increasingly rising phenomenon of the antibiotic resistance.

Example 4—Treatment of Patients Affected by Lesions of the Mucosa of the Oral Cavity A non-surgical treatment protocol and a surgical treatment protocol are disclosed below.

The non-surgical treatment protocol comprises the following steps:

Isolating the affected part with cylindrical cotton swabs;

Drying with a jet of air for a time of 10 seconds;

Through the use of a small brush, applying the composition according to the invention in the periodontal pocket around the tooth (in the case of periodontal disease), around the implant (in the case of perimplantitis) or on the aphtha;

Letting the composition to act for a period of 20 seconds;

Washing the treated zone with a flow of sterile water and simultaneously aspirating the liquid, so as to remove the composition completely;

The non-surgical treatment protocol comprises the following steps:

Performing local anaesthesia;

Proceeding with periodontal flap, consisting of the lifting of a portion of gingiva at the periodontal pocket;

Performing a surgical periodontal or peri-implant debridement;

Drying with a jet of air for 10 seconds;

Through the use of a small brush, applying the composition according to the invention in around the tooth (in the case of periodontal disease) or around the implant (in the case of perimplantitis);

Letting the composition to act for a period of 20 seconds;

Washing the treated zone with a flow of sterile water and simultaneously aspirating the liquid, so as to remove the composition completely;

Removing possible residues of purulent tissue.

The result obtained through the treatment protocols disclosed above can be verified both clinically (namely, by measuring the depth of the periodontal pocket in the non-surgically treated patients) and by carrying out microbiological tests before and after the treatment. Surprisingly, in 20 patients non surgically treated an immediate reduction of the periodontal pocket by about 50% was observed after the application of the composition according to the invention.

As a person skilled in the art will understand, variations on and/or additions to what has been disclosed above are possible. For example, although the previously disclosed compositions were prepared on laboratory scale, the person skilled in the art is able to provide preparation procedures that are suitable for a production on industrial scale.

The invention claimed is:

1. A method of removing biofilm and necrotic or infected tissues from skin lesions or lesions of the oral cavity, the method comprising:
applying a composition comprising methanesulfonic acid onto skin lesions or onto lesions of the oral cavity of a patient in need thereof and removing the biofilm or the necrotic or the infected tissues from said lesions.

2. The method of claim 1, wherein said methanesulfonic acid is methanesulfonic acid 99.0%.

3. The method of to claim 1, wherein the composition further comprises a proton acceptor.

4. The method of claim 3, wherein said proton acceptor is selected from the group consisting of: anhydrous sodium carbonate, 5-amino-2-mercaptobenzimidazole, ethylenediaminetetraacetic acid tetrasodium salt, sodium gluconate, sodium tartrate dihydrate, 2-mercapto-5-benzimidazole sodium sulfonate, dimethyl sulfoxide, polyethylene glycol 400, polyethylene glycol 600, silicon dioxide, tetraethoxysilane, and mixtures thereof.

5. The method of claim 1, wherein the composition is prepared in a form selected from the group consisting of: solution, gel and cream.

6. The method of claim 4, wherein the composition has the following formulation:

| | |
|---|---|
| Methanesulfonic acid anhydrous | 70-90% by weight |
| Sodium carbonate | 0.5-2% by weight |
| 5-amino-2-mercaptobenzimidazole | 1-2% by weight |
| Ethylenediaminetetraacetic acid tetrasodium salt | 1-6% by weight |
| Sodium gluconate | 1-6% by weight |
| Sodium tartrate dihydrate | 2-6% by weight |
| 2-mercapto-5-benzimidazole sodium sulfonate | 1-4% by weight. |

7. The method of claim 4, wherein the composition has the following formulation:

| | |
|---|---|
| Methanesulfonic acid | 70-90% by weight |
| 5-amino-2-mercaptobenzimidazole | 1-2% by weight |
| Ethylenediaminetetraacetic acid tetrasodium salt | 1-6% by weight |
| Sodium gluconate | 1-6% by weight |
| Sodium tartrate dihydrate | 2-6% by weight |

-continued

| | |
|---|---|
| 2-mercapto-5-benzimidazole sodium sulfonate | 1-4% by weight |
| Silicon dioxide | 0.1-7% by weight. |

8. The method of claim 4, wherein the composition has the following formulation:

| | |
|---|---|
| Methanesulfonic acid | 70-90% by weight |
| 5-amino-2-mercaptobenzimidazole | 1-2% by weight |
| Ethylenediaminetetraacetic acid tetrasodium salt | 1-6% by weight |
| Sodium gluconate | 1-6% by weight |
| Sodium tartrate dihydrate | 2-6% by weight |
| 2-mercapto-5-benzimidazole sodium sulfonate | 1-4% by weight |
| Silicon dioxide | 0.1-7% by weight |
| Tetraethoxysilane | 0.1-2% by weight. |

9. The method of claim 4, wherein the composition has the following formulation:

| | |
|---|---|
| Methanesulfonic acid | 70-90% by weight |
| Dimethyl sulfoxide | 10-30% by weight |
| Silicon dioxide | 0.1-7% by weight |
| Tetraethoxysilane | 0.1-2% by weight. |

10. The method of claim 4, wherein the composition has the following formulation:

| | |
|---|---|
| Methanesulfonic acid | 70-90% by weight |
| Sodium gluconate | 1-6% by weight |
| Sodium tartrate dihydrate | 2-6% by weight |
| Silicon dioxide | 0.1-7% by weight |
| Tetraethoxysilane | 0.1-2% by weight |
| Polyethylene glycol 400 or polyethylene glycol 600 | 1-10% by weight. |

11. The method of claim 4, wherein the composition has the following formulation:

| | |
|---|---|
| Methanesulfonic acid | 70-90% by weight |
| 5-amino-2-mercaptobenzimidazole | 1-8% by weight |
| Ethylenediaminetetraacetic acid tetrasodium salt | 1-8% by weight |
| 2-mercapto-5-benzimidazole sodium sulfonate | 1-8% by weight. |

12. The method of claim 1, wherein the composition, which is applied onto the lesions, comprises methanesulfonic acid in an amount of at least 70% by weight based on the weight of the composition.

* * * * *